(12) United States Patent
Long, Jr. et al.

(10) Patent No.: US 11,504,155 B2
(45) Date of Patent: Nov. 22, 2022

(54) SURGICAL GUIDANCE DEVICES, SYSTEMS, AND METHODS

(71) Applicant: Boston Scientific Scimed, Inc., Maple Grove, MN (US)

(72) Inventors: Jerry Timothy Long, Jr., Concord, MA (US); Timothy Paul Harrah, Cambridge, MA (US); Brandon W. Craft, Edgewater, MD (US); Elizabeth A. Stokley, Baltimore, MD (US); Sebastian Koerner, Berlin (DE); Anant Subramaniam, Baltimore, MD (US); Paul James Fearis, Owings Mills, MD (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 316 days.

(21) Appl. No.: 16/820,820

(22) Filed: Mar. 17, 2020

(65) Prior Publication Data
US 2020/0214738 A1 Jul. 9, 2020

Related U.S. Application Data

(63) Continuation of application No. 15/400,367, filed on Jan. 6, 2017, now Pat. No. 10,624,668.
(Continued)

(51) Int. Cl.
*A61B 17/34* (2006.01)
*A61B 5/06* (2006.01)
(Continued)

(52) U.S. Cl.
CPC .......... *A61B 17/3403* (2013.01); *A61B 5/062* (2013.01); *A61B 34/20* (2016.02);
(Continued)

(58) Field of Classification Search
CPC ..... A61B 17/3403; A61B 34/20; A61B 90/11; A61B 90/13; A61B 90/37;
(Continued)

(56) References Cited

U.S. PATENT DOCUMENTS

| 1,581,706 A | 4/1926 | White |
| 1,581,707 A | 4/1926 | White |

(Continued)

FOREIGN PATENT DOCUMENTS

| CN | 103635146 A | 3/2014 |
| CN | 104853799 A | 8/2015 |

(Continued)

OTHER PUBLICATIONS

International Search Report and Written Opinion for International Application No. PCT/US2017/012541, dated Mar. 23, 2017 (13 pages).

*Primary Examiner* — Christopher A Flory
(74) *Attorney, Agent, or Firm* — Bookoff McAndrews, PLLC.

(57) ABSTRACT

A guidance method comprising: placing a tracking pad adjacent a body, the tracking pad including a guiding opening and a plurality of sensors, locating a distal end of a needle inside of the guiding opening at an insertion point adjacent the body, the needle including at least one beacon, operating the plurality of sensors with the at least one beacon to track an actual disposition of the needle, establishing a target disposition for the needle, moving the needle in a direction of movement to synchronize the actual disposition with the target disposition, and inserting the distal end of the needle into the body along an insertion axis.

19 Claims, 10 Drawing Sheets

Related U.S. Application Data

(60) Provisional application No. 62/276,567, filed on Jan. 8, 2016.

(51) Int. Cl.

| | | |
|---|---|---|
| *A61B 90/13* | (2016.01) | |
| *A61B 90/00* | (2016.01) | |
| *A61B 34/20* | (2016.01) | |
| *A61B 90/11* | (2016.01) | |
| *A61B 17/00* | (2006.01) | |

(52) U.S. Cl.
CPC .............. *A61B 90/11* (2016.02); *A61B 90/13* (2016.02); *A61B 90/37* (2016.02); *A61B 2017/00039* (2013.01); *A61B 2017/00115* (2013.01); *A61B 2017/00199* (2013.01); *A61B 2017/00221* (2013.01); *A61B 2017/3407* (2013.01); *A61B 2017/3413* (2013.01); *A61B 2034/2051* (2016.02); *A61B 2034/2053* (2016.02); *A61B 2090/3945* (2016.02)

(58) Field of Classification Search
CPC .. A61B 2017/00039; A61B 2017/3407; A61B 5/062; A61B 2034/2051; A61B 2034/2053; A61B 2090/3945; A61B 2017/00115; A61B 2017/00199; A61B 2017/00221; A61B 2017/3413
See application file for complete search history.

(56) References Cited

U.S. PATENT DOCUMENTS

| | | |
|---|---|---|
| 1,581,708 A | 4/1926 | White |
| 1,581,709 A | 4/1926 | White |
| 1,581,710 A | 4/1926 | White |
| 2,451,077 A | 10/1948 | Emsig |
| 3,110,956 A | 11/1963 | Fischer, Jr. |
| 4,899,756 A | 2/1990 | Sonek |
| 5,592,939 A | 1/1997 | Martinelli |
| 5,758,650 A | 6/1998 | Miller et al. |
| 5,848,986 A | 12/1998 | Lundquist et al. |
| 5,871,446 A | 2/1999 | Wilk |
| 6,006,126 A | 12/1999 | Cosman |
| 6,607,529 B1 * | 8/2003 | Jones ................ A61B 18/1485 606/49 |
| 8,361,066 B2 | 1/2013 | Long et al. |
| 8,640,940 B2 | 2/2014 | Ohdaira |
| 2002/0052610 A1 | 5/2002 | Skakoon et al. |
| 2002/0111615 A1 | 8/2002 | Cosman et al. |
| 2002/0156372 A1 | 10/2002 | Skakoon et al. |
| 2006/0079885 A1 | 4/2006 | Rick |
| 2007/0250075 A1 | 10/2007 | Skakoon et al. |
| 2007/0250076 A1 | 10/2007 | Skakoon et al. |
| 2007/0250077 A1 | 10/2007 | Skakoon et al. |
| 2007/0255275 A1 | 11/2007 | Skakoon et al. |
| 2008/0082108 A1 | 4/2008 | Skakoon et al. |
| 2008/0269602 A1 | 10/2008 | Csavoy et al. |
| 2009/0053003 A1 | 2/2009 | Clark |
| 2009/0062788 A1 | 3/2009 | Long et al. |
| 2009/0306652 A1 | 12/2009 | Buysse et al. |
| 2010/0179530 A1 | 7/2010 | Long et al. |
| 2010/0292686 A1 | 11/2010 | Rick et al. |
| 2011/0022058 A1 | 1/2011 | Skakoon et al. |
| 2011/0022059 A1 | 1/2011 | Skakoon et al. |
| 2011/0258843 A1 | 10/2011 | Dukesherer et al. |
| 2011/0282188 A1 | 11/2011 | Burnside et al. |
| 2011/0295108 A1 | 12/2011 | Cox et al. |
| 2012/0143029 A1 | 6/2012 | Silverstein et al. |
| 2012/0149982 A1 | 6/2012 | Fonger et al. |
| 2013/0006102 A1 | 1/2013 | Wilkes et al. |
| 2013/0066192 A1 | 3/2013 | Sarvestani et al. |
| 2014/0031674 A1 | 1/2014 | Newman et al. |
| 2014/0046261 A1 | 2/2014 | Newman et al. |
| 2014/0107475 A1 | 4/2014 | Cox et al. |
| 2014/0163356 A2 | 6/2014 | Burnside et al. |
| 2015/0100064 A1 | 4/2015 | Skakoon et al. |
| 2015/0297114 A1 | 10/2015 | Cox et al. |
| 2017/0020561 A1 | 1/2017 | Cox et al. |
| 2017/0079548 A1 | 3/2017 | Silverstein et al. |
| 2017/0079681 A1 | 3/2017 | Burnside et al. |
| 2018/0168559 A1 | 6/2018 | Hautvast et al. |
| 2019/0117187 A1 | 4/2019 | Patel et al. |

FOREIGN PATENT DOCUMENTS

| | | |
|---|---|---|
| CN | 105662402 A | 6/2016 |
| EP | 2567668 A1 | 3/2013 |
| JP | 2002-502276 A | 1/2002 |
| JP | 2003-260064 A | 9/2003 |
| JP | 2005-323669 | 11/2005 |

\* cited by examiner

SURGICAL GUIDANCE DEVICES, SYSTEMS, AND METHODS

CROSS-REFERENCE TO RELATED APPLICATION(S)

This patent application is a continuation under 37 CFR § 1.53(b) of U.S. application Ser. No. 15/400,367, filed Jan. 6, 2017, which claims the benefit of priority under 35 U.S.C. § 119 to U.S. Provisional Patent Application No. 62/276,567, filed Jan. 8, 2016, the disclosure of all of which are herein incorporated by reference in their entireties.

TECHNICAL FIELD

Aspects of the present disclosure generally relate to medical devices and procedures. In particular, some aspects relate to surgical guidance devices, systems and methods.

BACKGROUND

Non-invasive surgical procedures advantageously allow a surgeon to treat an internal area of a body without having to create a large physical opening in the exterior skin of the body. Many non-invasive procedures are specialized to treat a particular area of the body, such as an organ. Percutaneous nephrolithonomy (or "PCNL"), for example, is one such procedure, wherein an object, such as a needle, is inserted through the body and into a kidney for removal of a kidney stone. Precise placement of the needle is required to avoid damaging the kidney. Therefore, medical imaging techniques, such as fluoroscopy, may be used in PCNL procedures to both locate a kidney and track the location of the needle with respect to the located kidney.

Many imaging technologies are limited to producing an image of the body within a single imaging plane. For fluoroscopy, the imaging plane is defined with respect to the imaging plane of an x-ray beam. These technologies may be used to locate an organ, and determine a distance between an object and the organ; however, they are often ill-suited for guiding the object to the organ. For example, a PCNL needle may be pushed out of the imaging plane by bodily tissue, requiring the surgeon to either reposition the imaging plane with respect to the needle and the kidney, which is time consuming; or navigate the body based solely on tactile sensation, which is imprecise and potentially harmful to the body. Moreover, because many of these imaging technologies produce a two dimensional image of a three dimensional body, they may skew or blur the geometrical relationship between the object and the body. In PCNL procedures, for example, these limitations can make it difficult for the surgeon to determine whether the needle is being advanced towards the kidney along a desired insertion angle.

SUMMARY

Aspects of the present disclosure are related to surgical guidance devices, systems, and methods. Numerous aspects of the present disclosure are now described.

One aspect is a guidance device. An exemplary guidance device may comprise: a tracking pad with a guiding opening, and a plurality of sensors operable with at least one beacon on a needle to track the disposition of the needle at least when a distal end of the needle is inserted into the guiding opening.

According to this aspect, the at least one beacon may include a magnetic element, and each of the plurality of sensors may be a transducer. For example, each transducer may be a Hall effect sensor. The tracking pad may define three positions arranged triangularly about the guiding opening, and the plurality of sensors may comprise at least one sensor placed at each of the three positions. The device may further comprise a marking element configured to indicate a target insertion point, inside the guiding opening, for the distal end of the needle. For example, the marking element may be configured to project at least two beams of light into the guiding opening, and the target insertion point may be indicated by a point of intersection between the at least two beams of light.

The plurality of sensors may be configured to determine an actual insertion point, inside the guiding opening, of the distal end of the needle. The plurality of sensors also may be configured to determine an actual insertion angle of the needle relative to the opening. In some aspects, the device may further comprise a guiding element on the tracking pad that indicates whether the actual insertion angle aligns with a target insertion angle. For example, the guiding element may comprise a plurality of indicators, each indicator being configured to indicate a direction of movement for aligning the actual insertion angle with the target insertion angle. The plurality of sensors may be further configured to determine the distance between the guiding opening and the distal end of the needle when the distal end is inserted into the opening.

The at least one beacon may comprise a first beacon located at the distal end of the needle and a second beacon located at a proximal end of the needle, wherein the disposition of the needle is tracked relative to either or both of the first and second beacons. In some aspects, the device may further comprise a transmitter configured to communicate an actual disposition of the needle to a processor, a receiver configured to receive a target disposition of the needle from the processor, and a guiding element configured to indicate a direction of movement for synchronizing the actual disposition with the target disposition. The guiding element may comprise a display configured to show the actual disposition relative to the target disposition; and/or the processor may be configured to establish the direction of movement and activate the guiding element.

Another aspect is another guiding device. According to this aspect, an exemplary guiding device may comprise a tracking pad with a guiding opening, and a plurality of sensors operable with at least one portion of a needle to generate a motion signal at least when a distal end of the needle is inserted into the guiding opening.

At least one portion of the needle may include a magnetic element, and each of the plurality of sensors may include a transducer operable with the magnetic element to generate the motion signal. For example, each transducer may be Hall effect sensor. The proximal end of the needle may include an interface with a polygonal gripping surface engageable with a forceps, and the device may further comprise a marking element configured to indicate a target insertion point, inside the guiding opening, for the distal end of the needle. The motion signal may communicate an actual insertion angle for the needle relative to guiding opening, wherein the device may further comprise a first guiding element configured to indicate a direction of movement for synchronizing the actual insertion angle with a target insertion angle. The motion signal also may communicate an actual distance between the guiding opening and the distal end of the needle, wherein the device further comprises a second guiding element configured to indicate when the actual distance approaches a target distance. For example, the plurality of sensors may be in communication with a processor configured to determine the target insertion point, the target insertion angle, and the target distance, and activate the first and second guiding elements.

Yet another aspect is a guidance system. An exemplary guidance system may comprise: a needle with at least one beacon; a tracking pad with a guiding opening and a plurality of sensors operable with the at least one beacon to track the disposition of the needle when the distal end of the needle is inserted into the guiding opening; a transmitter configured to communicate an actual disposition of the needle to a processor; a receiver configured to receive a target disposition of the needle; and a guiding element configured to indicate a direction of movement for synchronizing the actual disposition of the needle with the target disposition of the needle.

In this aspect, the guiding element may comprise a display configured to show the actual disposition of the needle and the target disposition of the needle. The guiding element may further comprise a plurality of indicators on the tracking pad. Each indicator may be configured to indicate the direction of movement for the needle. The system may further comprise an access guide comprising a base attached to the tracking pad, the base including an opening coaxial with the guiding opening, and a holder moveably attached to the base. For example, the holder may include a bore configured to receive the needle and define the insertion axis. The system may further comprise a probe that is attached to the base or the holder, and/or configured to generate a motion signal when the needle is inserted through the bore along the insertion axis. The system may further comprise a probe with a base sized for receipt within the guiding opening of the pad. For example, the probe may be configured to generate a motion signal when the needle is inserted through the bore along the insertion axis. The image may be generated in an imaging plane of the probe.

Still yet another aspect is a guidance method. An exemplary guidance method may comprise: placing a tracking pad adjacent a body, the pad including a guiding opening and a plurality of sensors; locating a distal end of a needle inside of the guiding opening at an insertion point adjacent the body, the needle including at least one beacon; operating the plurality of sensors with the at least one beacon to track the actual disposition of the needle; establishing a target disposition; moving the needle in a direction of movement to synchronize the actual disposition with the target disposition; and inserting the distal end of the needle into the body along an insertion axis.

The tracking pad may include a marking element configured to establish a target insertion point inside the guiding opening of the pad, wherein the method further comprises establishing the target insertion point, and placing the distal end of the needle adjacent the target insertion point. The plurality of sensors may be configured to track an actual insertion angle of the needle relative to the guiding opening, wherein the method further comprises establishing a target insertion angle, and moving the needle so as to align the actual insertion angle with the target insertion angle. The plurality of sensors may be further configured to track the distance between the guiding opening and the distal end of the needle relative to the guiding opening, wherein the method further comprises establishing a target distance between the guiding opening and the distal end of the needle, and inserting the distal end of the needle into the body until the target distance is obtained.

In some aspects, the method may comprise recalibrating the plurality of sensors to define the target distance after moving the needle so as to align the actual insertion angle with the target insertion angle. The method may further comprise transmitting the actual disposition of the needle to a processor; receiving a target disposition for the needle from the processor; and indicating a direction of movement for the needle with a guiding element associated with the tracking pad.

It may be understood that both the foregoing summary and the following detailed description are exemplary and explanatory only, neither being restrictive of the present disclosure unless claimed below.

BRIEF DESCRIPTION OF THE DRAWINGS

The accompanying drawings, which are incorporated in and constitute a part of this specification, illustrate exemplary aspects that, together with the written descriptions, serve to explain the principles of this disclosure.

DETAILED DESCRIPTION

The present disclosure is now described with reference to exemplary aspects of a system for tracking the location of an object relative to a body. Some aspects are described with reference to a procedure using an elongated object, while other aspects incorporate a medical imaging technology. For example, some aspects may be depicted and/or described with reference to the tracking of a needle relative to a kidney. Any reference to a particular procedure (such as PCNL), object (such as a needle), area of the treatment (such as a kidney), or medical imaging technology (such as x-ray) is provided for convenience and not intended to limit the present disclosure. Accordingly, the concepts and novelty underlying each aspect may be utilized for or with any analogous type of procedure, object, area of treatment, or imaging technology, medical or otherwise.

Numerous axes are described below, for example, with reference to an opening having an axis Y-Y transverse therewith. These directional terms are provided to establish a coordinate system with reference to the present disclosure. The directional terms "proximal" and "distal" are used herein to refer to the relative components and features of the present disclosure. The term proximal refers to a position closer to the exterior of the body or a user, whereas the term distal refers to a position closer to the interior of the body or further away from the user. The term "elongated" as used herein refers to any object that is substantially longer in relation to its width, such as an object having a length that is at least two times longer than its width. Some elongated objects, for example, are axially extending in a proximal or distal direction along an axis. Unless they appear in the appended claims, such terms are provided for convenience and not intended to limit the present disclosure.

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

Figure 2:
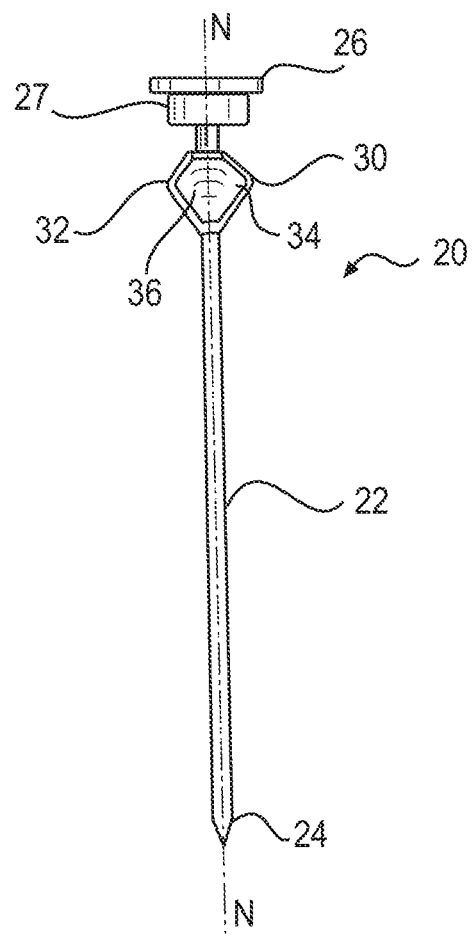
FIG. 2 is a profile view of an exemplary aspect of a needle in accordance with the present disclosure.
Figure 3:
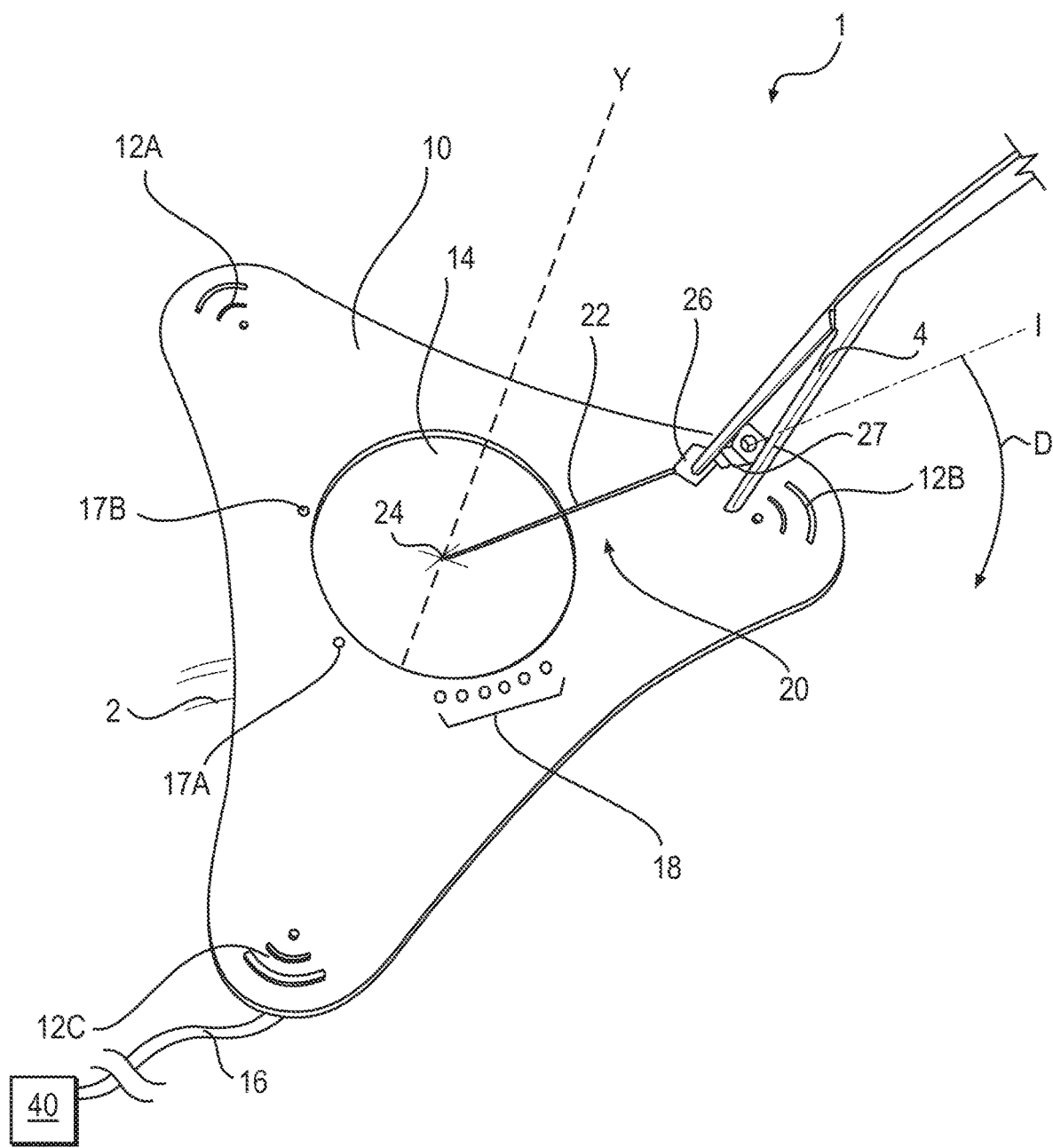
FIG. 3 is a perspective view of an exemplary system according to the present disclosure, wherein the system comprises the tracking pad of FIG. 1A together with the needle of FIG. 2.

One aspect of the present disclosure is depicted in FIG. 3 as a system 1. In this aspect, system 1 comprises a tracking pad 10 (FIGS. 1A-B); and a needle 20 (FIG. 2). Pad 10 is depicted as a substantially planar, flexible element having a triangular shape with a plurality of sensors, such as a sensor 12A, a sensor 12B, and a sensor 12C (or sensors 12A-C), and at least one guiding opening 14. The plurality of sensors are operable to track the disposition of needle 20 relative to opening 14. Sensors 12A-C may, for example, be configured to track, in real time, both the location of a distal end 24 of needle 20 inside of guiding opening 14, and the actual insertion angle of needle 20 relative to opening 14. Each element of system 1 is now described.

Figure 1A:
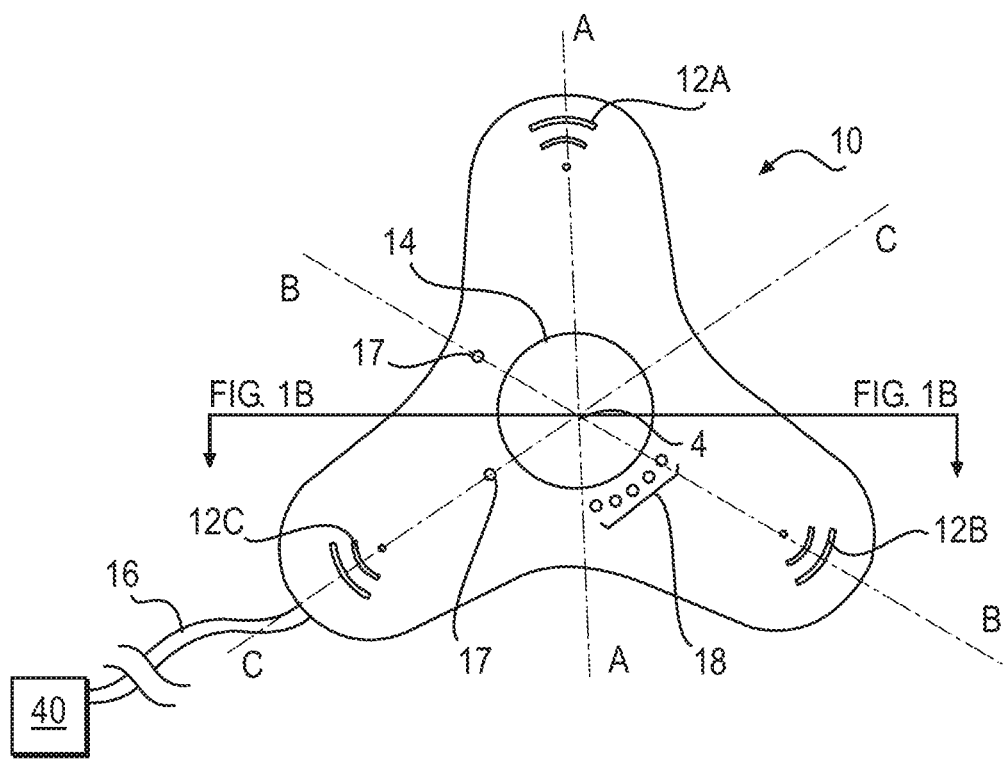
FIG. 1A is a plan view of an exemplary aspect of a tracking pad in accordance with the present disclosure.
Figure 1B:
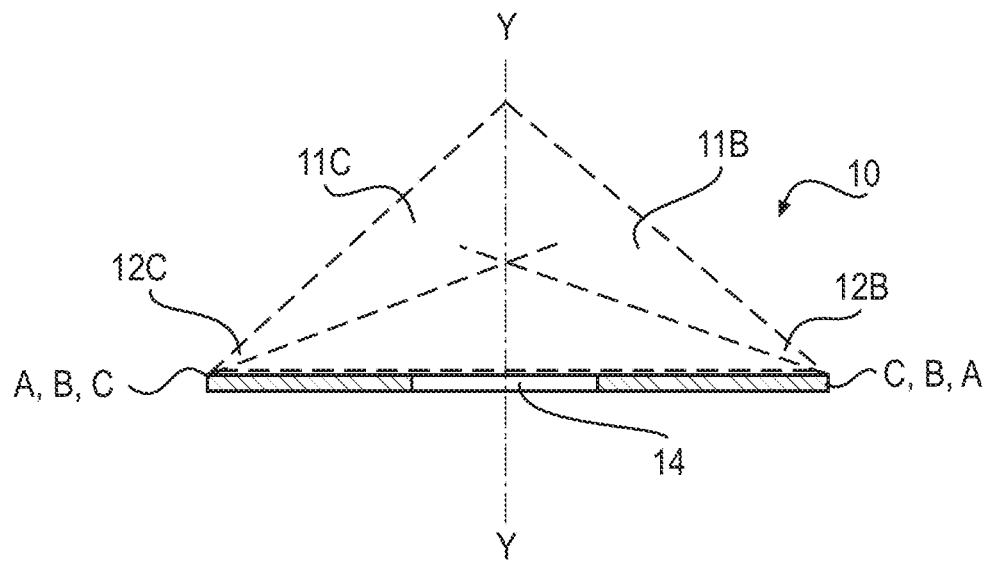
FIG. 1B is a section view of the tracking pad of FIG. 1A.

As shown in FIG. 1A, sensors 12A-C are located in a triangular arrangement about guiding opening 14. Each sensor has a detection field oriented toward an axis Y-Y transverse with opening 14, as shown in FIG. 1B, where sensors 12B and 12C have, respectively, a detection field 11B or 11C oriented toward axis Y-Y. Sensors 12A-C are configured to track the disposition of needle 20 using any triangulation technique known in the art. Each sensor 12A-C is depicted as a transducer, such as a Hall-effect sensor. As is known, Hall effect sensors generate a measurable voltage when subjected to a magnetic flux perpendicular to the flow of an electric current across the sensor. This measureable voltages output from each sensor 12A-C are referred to as a motion signal herein. Accordingly, pad 10 may be utilized to track, by triangulation, the disposition of needle 20 using the motion signals output from sensors 12A-C.

Tracking pad 10 has one or more marking elements 17 configured to establish a target insertion point for the distal end 24 of needle 20. As shown in FIGS. 1A and 3, an exemplary marking element 17 is depicted as a first indicator 17A disposed relative to a second indicator 17B about the perimeter of guiding opening 14. Each indicator 17A and 17B may, for example, be an LED configured to project a beam of light into opening 14, wherein the target insertion point is defined by the intersection of the beams of light. Pad 10 has a guiding element 18 configured to indicate whether needle 10 is inserted into opening 14 at a targeted insertion angle and, if necessary, communicate a direction of correction (shown by arrow "D" in FIG. 3). Guiding element 18 of FIG. 3 comprises a plurality of indicators disposed around the perimeter of opening 14. These indicators may, for example, be a plurality of LEDs configured to light up at full intensity to indicate when a correction is required, and then generate a trailing or leading arc length of varying intensity or frequency to indicate a direction for said correction.

A cable 16 extends away from pad 10 in FIGS. 1A and 3. Cable 16 is depicted as a power source and transceiver for device 10. For example, cable 16 may be utilized to power sensors 12A-C, marking element 17, and guiding element 18; transmit motion signals from sensors 12A-C to a processor 40; and receive one or more guiding signals from processor 40. In this disclosure, processor 40 may be, or be part of, any known computing device, such as a personal computer, smartphone, server, or the like. By leveraging processor 40 to perform the aforementioned tracking and guiding functions, pad 10 is simplified. Numerous benefits may be realized by this configuration. For example, as shown in FIG. 3, sensors 12A-C may be sealed within pad 10 to prevent fluid contamination and permit sterilization. Making processor 40 external also makes pad 10 more durable and less expensive to manufacture.

An exemplary needle 20 is illustrated in FIG. 2 as having an elongated body 22 extending along a needle axis N-N between distal end 24 and a proximal end 26. Needle 20 may be any type of elongated object, such as a cannula, catheter with one or more working channels, a rigid or flexible tube, or like element. For example, in FIG. 2, distal end 24 has a sharpened tip configured to penetrate bodily tissue. Proximal end 26 has an interface 27 engageable with a manipulation tool. For example, interface 27 of FIG. 3 is depicted as a portion of proximal end 26 having a polygonal shape engageable with a forceps 4. Proximal end 26 may assume any suitable shape, such as circular of spherical shape, which may have a portion configured for use with forceps 4, such as interface 27. Other aspects of needle 20 may have a interface 27 with a gripping surface configured for use with a hand (as in FIG. 8).

At least one beacon 30 is attached to needle 20. In FIG. 2, a single beacon 30 is adjacent proximal end 26. Beacon 30 has an exterior surface 32 depicted as a surface of revolution about axis N-N. An interior volume 34 of beacon 30 is defined between exterior surface 32 and needle 20. In this aspect, a magnetic element 36 is mounted inside of interior volume 34 and depicted as another surface of revolution about axis N-N, one that is offset uniformly from exterior surface 32. The symmetrical shape of element 36 may be configured to generate a magnetic field with uniform flux density, thereby improving the consistency of any motion signals generated therefrom by sensors 12A-C. Magnetic element 36 may be formed of any magnetic material known in the art, including any material composed of one or more rare earth metals. Exterior surface 32 may be a conformal protective layer applied to element 36.

As shown in FIG. 3, when system 1 is in use, sensors 12A-C are operable with the at least one beacon 30 to track the disposition of needle 20 when distal end 24 is inserted into opening 14 along an insertion axis transverse to opening 14. As noted above, sensors 12A-C are depicted as three Hall effect sensors, each being operable with the magnetic element 36 inside of beacon 30 to generate a motion signal. The motion signals will vary according to the disposition of beacon 30 relative to sensors 12A-C. For example, placing distal end 24 in opening 14, and then leaning beacon 30 towards sensor 12A (FIG. 1) will cause sensor 12A to interact with magnetic element 36, thereby generating a motion signal that varies from the signal generated by sensors 12B and 12C. Other motions signals are produced by leaning beacon 30 towards one of the other sensors 12B or 12C, or in an intermediate direction. In some aspects, each motion signal is fed into processor 40, which then tracks the disposition of needle 20 in real-time, as described more fully in the method steps below.

Figure 4A:
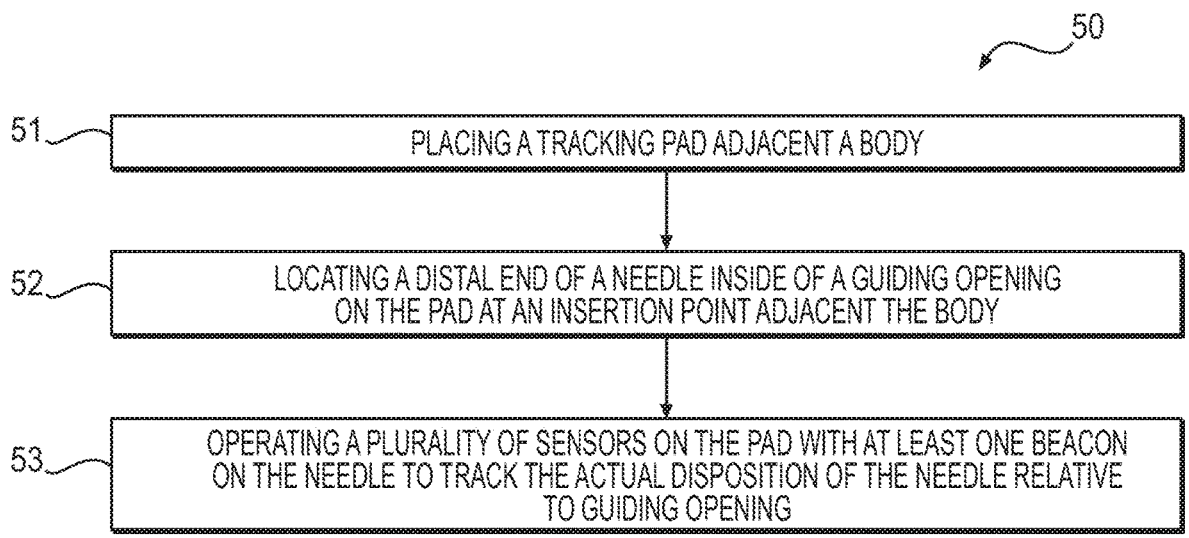
FIG. 4A depicts an exemplary set of method steps.

Methods of using system 1 of FIG. 3 are now described. An exemplary tracking method 50 may comprise the step 51 (FIG. 4A) of placing a tracking pad 10 adjacent a body 2, wherein pad 10 has a guiding opening 14 and a plurality of sensors 12A-C. Step 51 may further comprise plugging cable 16 into an external power source and/or placing cable 16 in communication with processor 40. Another method step 52 (FIG. 4A) may comprise locating a distal end 24 of a needle 20 inside of guiding opening 14 at an insertion point adjacent body 2, wherein needle 20 has at least one beacon 30 attached thereto. If manufactured separately, then step 52 may further comprise attaching beacon 30 to needle 20. Another method step 53 (FIG. 4A) may comprise operating sensors 12A-C with the at least one beacon 30 to track the actual disposition of needle 20 relative to opening 14.

Figure 4B:
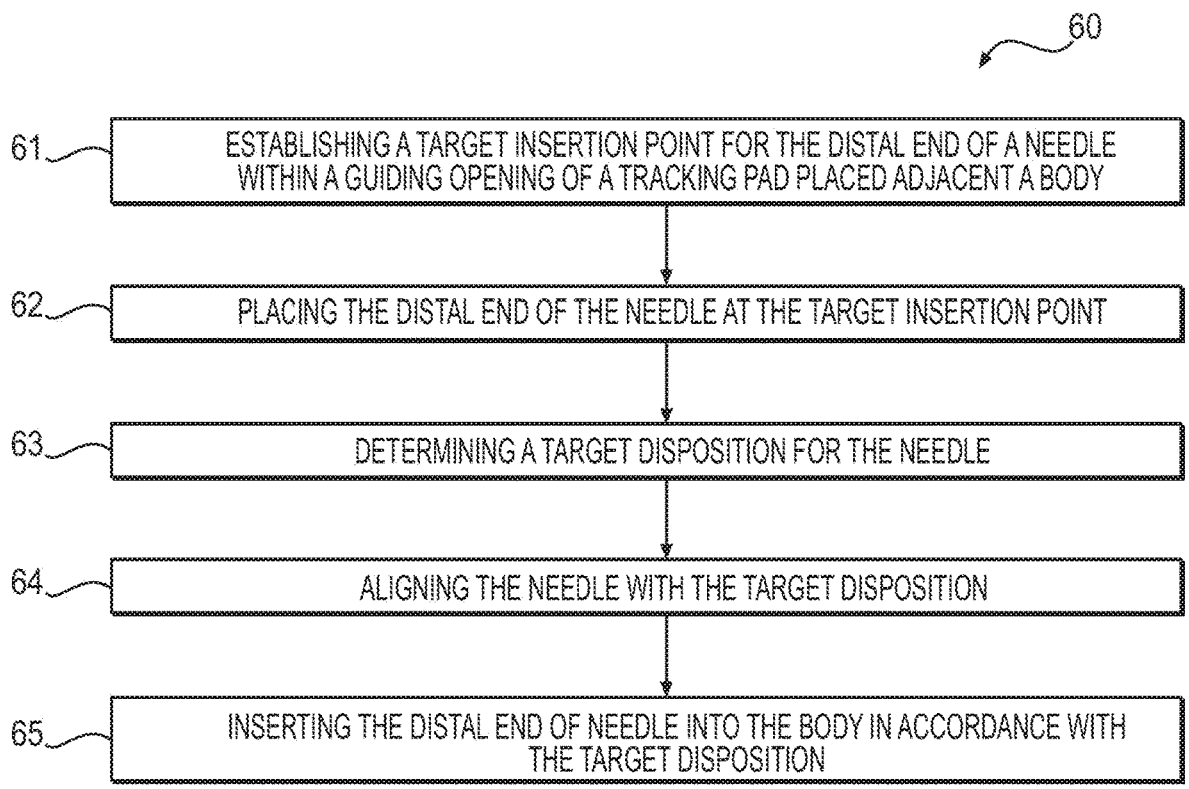
FIG. 4B depicts another exemplary set of method steps.

An exemplary guiding method 60 is also disclosed. In addition to the steps described above, method 60 may comprise a step 61 (FIG. 4B) for establishing a target insertion point for the distal end 24 of needle 20 within guiding opening 14 of pad 10; and a step 62 (FIG. 4B) for placing distal end of 24 at the target insertion point. In addition, or alternatively, method 60 may further comprise a step 63 (FIG. 4B) for determining a target disposition for needle 20; a step 64 (FIG. 4B) for aligning needle 20 with the target disposition; and a step 65 (FIG. 4B) for inserting distal end 24 of needle 20 into body 2 in accordance with the target disposition.

Alternative aspects of system 1 and their associated methods are also disclosed, each aspect being part of the present disclosure. Tracking pad 10, for example, is described as a triangular, flexible element, yet may assume any shape or rigidity. Although depicted as circular in FIG. 1, the perimeter of guiding opening 14 may assume any geometric shape, regular or irregular, closed or open. Guiding opening 14 may further comprise a self-sealing membrane configured to prevent fluids from leaking into or out of body 2. For example, such a membrane could be attached to a distal surface of pad 10 so as to span opening 14. This membrane could be a first membrane attached to a distal surface of pad 10, and a second membrane attached to a proximal surface of pad, thereby creating an interstitial space configured to trap unwanted fluids between the first and second membranes. Although described as a single element, pad 10 may be separated into, for example, three distinct elements, each containing one or more of sensors 12A-C, wherein each distinct element is linked by wired or wireless connection to a power source and a transceiver similar to those described above. These distinct elements could also be linked by a connective membrane, such as the self-any of the sealing membranes described above.

Sensors 12A-C have been described as Hall effect sensors coupled to pad 10, but this is not required. For example, to generate a motion signal according to the present disclosure, one or more of sensors 12A-C may alternatively be a sensing coil that utilizes magnetic fields, such as those based on very low frequencies, induction balancing, pulsed induction, beat-frequency oscillators, or like technologies. Any of sensors 12A-C may also be a radar sensor that utilizes sound waves, a lidar sensor that utilizes laser energy, an optical sensor that utilizes shape or signal recognition, or any other type of known sensing technology suitable for use in accordance with this disclosure. Any number of sensors, or combination of sensor types may be used.

Beacon 30 may be configured to operate with any sensor type, including those described herein. For example, beacon 30 may be a made of a conductive material with a inductance and/or resistance suitable for use with sensors 12A-C. Alternatively, beacon 20 may have a reflective surface configured to reflect sound waves or lasers, or a coded surface readable by an optical sensor. Alternatively still, beacon 30 may be a coil, a small resonant RC circuit, or even a magnetostrictive element that is momentarily excited by sensors 12A-C, activating briefly to provide and excite a magnetic field. Either beacon 30 or sensors 12A-C may generate a motion signal by listening for the inductively activated resonant signal to settle, and then measure time of flight or resonant signal strength. In this regard, beacon 30 may be an active, albeit non-powered element of needle 20. Beacon 30 may also be a powered element. For example, although described as solid, magnetic element 36 may be an electromagnetic coil that is powered to, for example, produce a stronger magnetic field.

Needle 20 of FIG. 2, for example, is depicted has having a single beacon 30. This is not required. Instead, needle 20 may have a first beacon at distal end 24 and a second beacon at proximal end 26, thereby allowing sensors 12A-C to track the disposition of either or both of the first or second beacons 30 relative to guiding opening 14. In this aspect, sensors 12A-C may be modified or positioned so that their respective detection fields (FIG. 1B) are expanded to each side of pad 10. Beacon 30 may be located inside a hollow portion of needle 20, or manufactured as an accessory attachable to a needle 20.

Cable 16 may also be modified. For example, in some aspects, pad 10 may comprise a wireless transceiver, such as a radio frequency transceiver, configured to send/receive the signals to/from processor 40, such that cable 16 is used exclusively as a power source for each element of pad 10. In still other aspects, Pad 10 may further comprise an internal battery so as to eliminate cable 16 entirely.

Processor 40 is described as a separate element, but may integral with pad 10. For example, processor 40 may be housed inside of pad 110. As noted above, any aspect of processor 40 may be used to receive motion signals from sensors 12A-C and track, via triangulation, the disposition of needle 20. Any number of sensors may be used. Thus, processor 40 may be configured to utilize the additional motion signals within any location determining algorithm.

Methods 50 and 60 may be modified for use with processor 40. For example, method 50 (FIG. 4A) may alternatively comprise a step for sending, with cable 16, a motion signal from sensors 12A-C to a processor 40; and a step for tracking, with processor 40, the disposition of needle 20. As a further example, method 60 may alternatively comprise a step for establishing, with processor 40, the target insertion point; a step for communicating, with processor 40, the target insertion point to a market element 16; and a step for indicating, with marking element 17, the target insertion point. Likewise, method 60 (FIG. 4B) may alternatively comprise a step for determining, with processor 40, the target disposition; a step for communicating, with processor 40, the target disposition to guiding element 18; and a step for indicating, with guiding element 18, a direction of movement for aligning needle 20 with the target disposition.

Additional aspects of the present disclosure are now described with reference to a system 100, a system 200, a system 300, and associated methods. Wherever possible, each element of systems 100, 200, and 300 is described using reference numbers similar to those of system 1. Any feature described with reference to systems 100, 200, or 300 may be combined with any feature described with reference to system 1, each potential variation being an exemplary aspect.

Figure 5A:
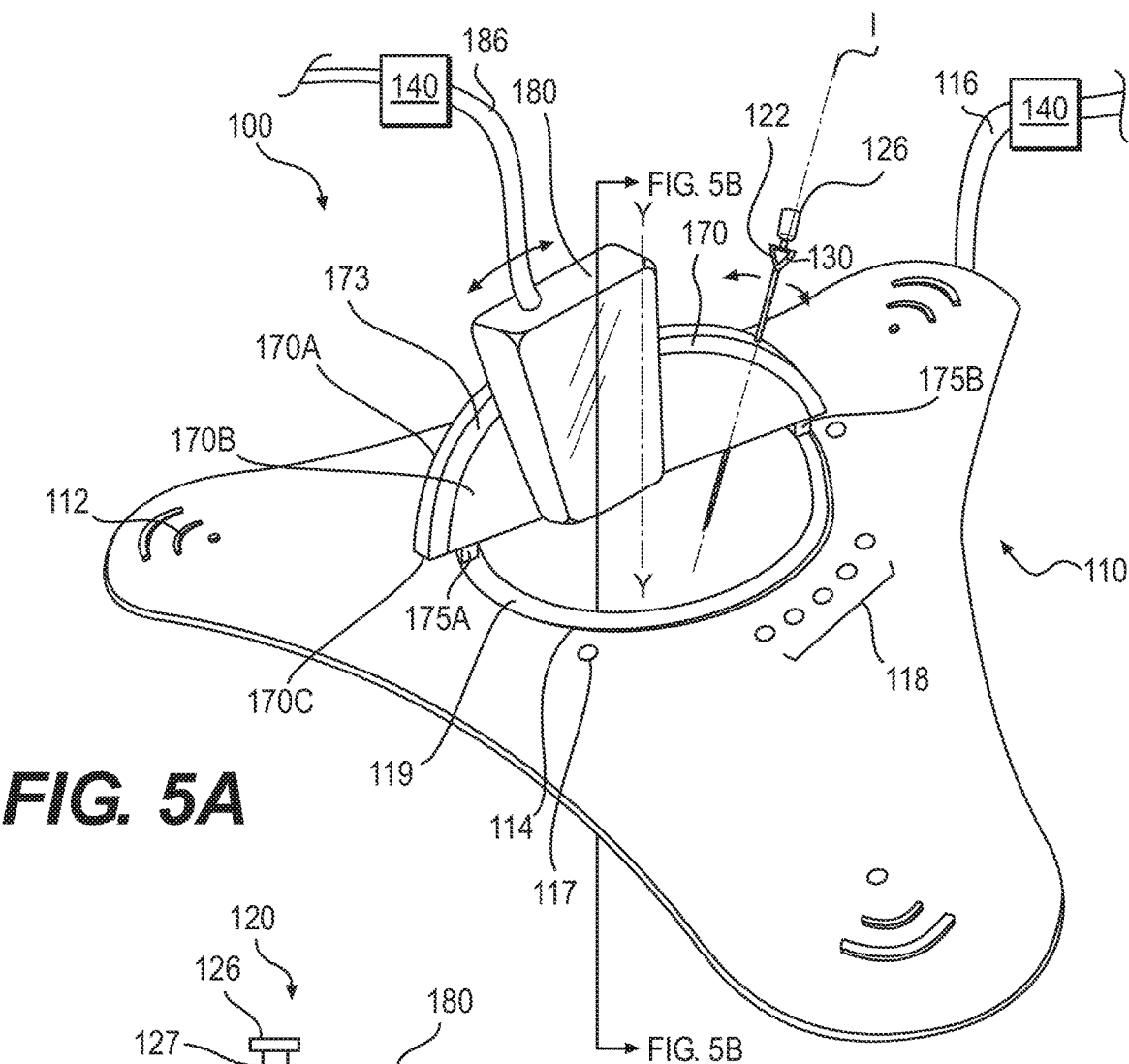
FIG. 5A is a perspective view of another exemplary system according to the present disclosure, the system comprising a tracking pad, a needle, and an access guide.
Figure 5B:
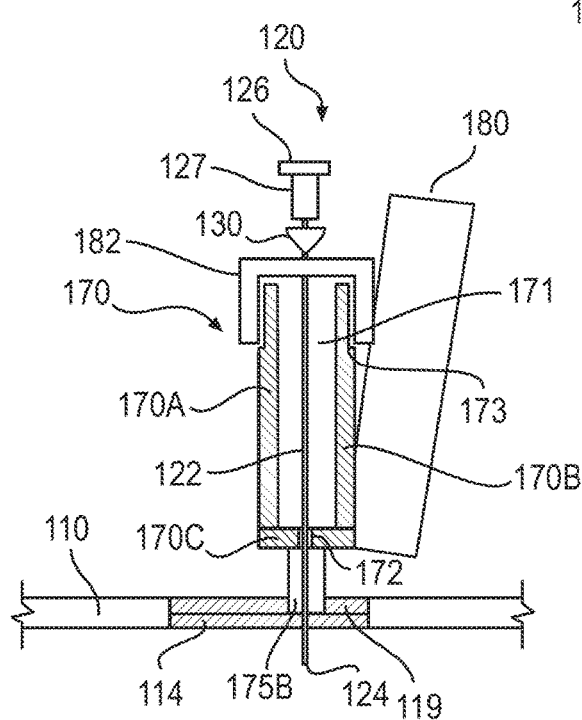
FIG. 5B is a section view of the system of FIG. 5A.
Figure 6:
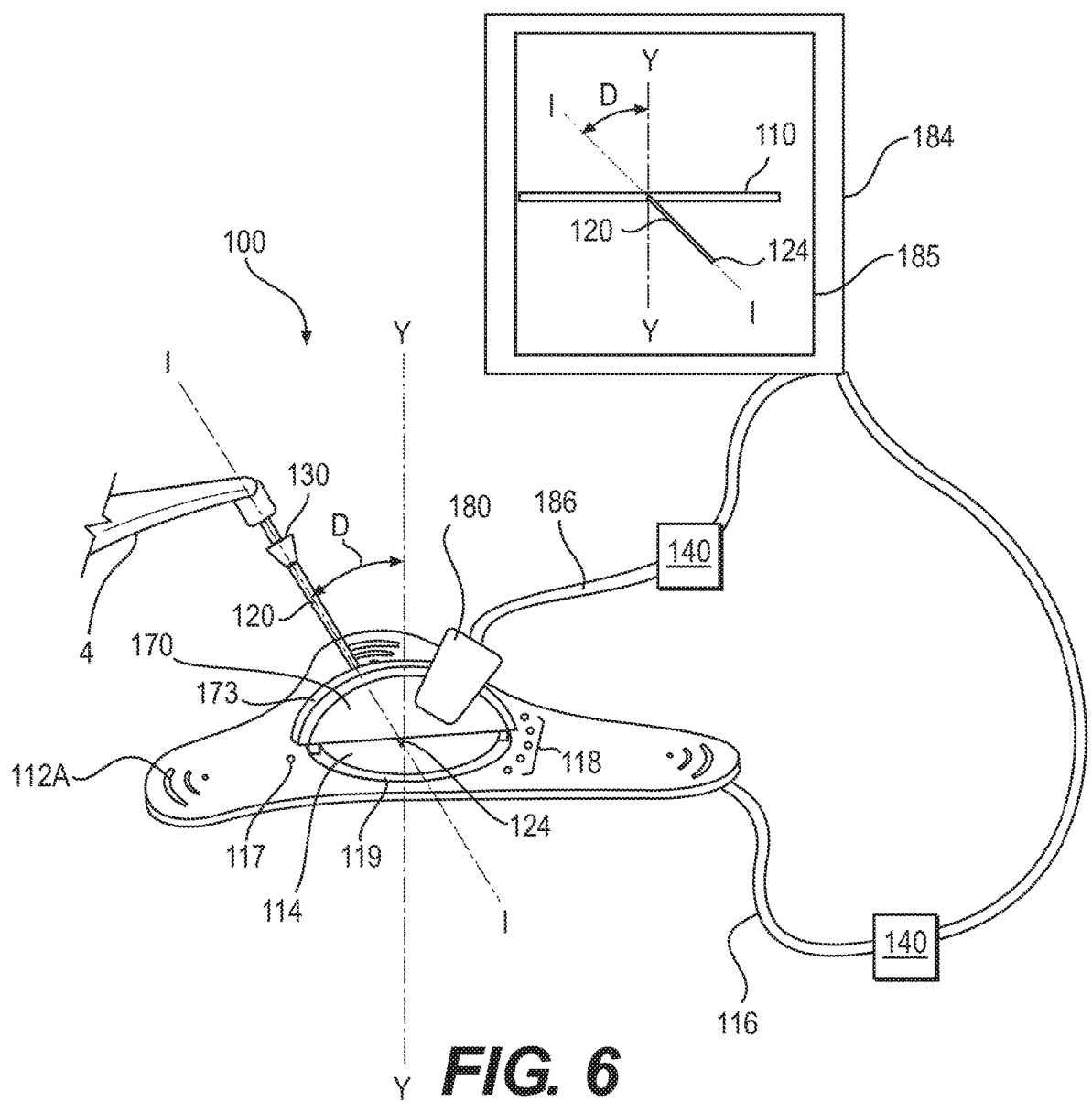
FIG. 6 is a perspective view of the system of FIG. 5A, wherein the system further comprises a display.

System 100 is depicted in FIGS. 5A-B and 6 as comprising a tracking pad 110 and a needle 120. Similar to above, pad 110 has a plurality of sensors 112, at least one guiding opening 114, a marking element 117, and a guiding element 118. System 100 further comprises an access guide 170 movably attached to pad 110. Guide 170 of FIGS. 5A-B, for example, is configured to receive a probe 180 and needle 120 so as to ensure that needle 120 will remain in the imaging plane of probe 180. Probe 180 is depicted as an ultrasonic probe that, like sensors 112, communicates a motion signal in response to needle 120. As shown, needle 120 has at least one beacon 130 operable with the plurality of sensors 112 to track the disposition of needle 120 when a distal end 124 (FIG. 5B) of needle 120 is inserted into opening 114, through guide 170, along an insertion axis I-I transverse to opening 114.

As shown in FIG. 5B, access guide 170 has a U-shaped cross-section defined by a first surface 170A, a second surface 170B, and a base surface 170C connecting first and second surfaces 170A and 170B. Base surface 170C has a width greater than the diameter of needle 120, thereby defining a guide channel 171. In one aspect, a guide hole 172 is provided in base surface 170C. Guide hole 172 may have a beveled edge and a diameter greater than the diameter of needle 120. Needle 120 may be inserted through channel 171, into hole 172, and then rotated with respect to axis Y-Y without leaving a plane defined by channel 171. Needle 120 may, thus, be pivoted in channel 171 without leaving the imaging plane of probe 180. As shown in FIGS. 5A-B, a proximal edge of first and second surfaces 170A and 170B defines a track 173 engageable with an interface structure 182 of probe 180. Interface structure 182 is slidably engageable with track 173 so that probe 180 can be rotated with respect to axis Y-Y. Accordingly, probe 180 is depicted as having a range of motion that allows the surgeon to adjust the position of the imaging plane relative to needle 120.

The disposition of needle 120 and probe 180 may also be adjusted. Access guide 170 of FIG. 6, for example, is rotatable with respect to pad 110 about axis Y-Y. As shown, pad 110 has a track 119 adjacent the perimeter of opening 114. Base surface 170C of guide 170 has a pair of protrusions 175A and 175B extending distally therefrom. Protrusions 175A and 175B may be snapped into track 119, allowing guide 170 to be rotated about axis Y-Y. Guide 170 of FIG. 6 may also be pivotable with respect to pad 110. For example, each protrusion 175A and 175B may have a hinge that allows guide 170 to pivot relative to pad 110 in a direction transverse to axis Y-Y. A locking mechanism may be provided on pad 110 or protrusions 175A, 175B to fix the angle or position of guide 170 on pad 110.

As shown in FIG. 5-6, system 100 has cable 116 extending away from pad 110. Similar to above, cable 116 may be used to power sensors 112, marking element 117, and guiding element 118, and/or place each of those elements in communication with a processor 140. Probe 180 utilizes a cable 186 extending therefrom for a similar purpose. Accordingly, cable 116 may be used to communicate a first set of motion signals from plurality of sensors 112 to a processor 140, while cable 186 is used to communicate a second set of motion signals from probe 180 to processor 140. Processor 140 may be any computing device, including those listed above. In contrast to above, processor 140 of FIG. 6 is also in communication with a display 184 and may be used to generate a graphical representation 185 of the disposition of the needle 120 on display 184, as described further in the method steps below.

Figure 7:
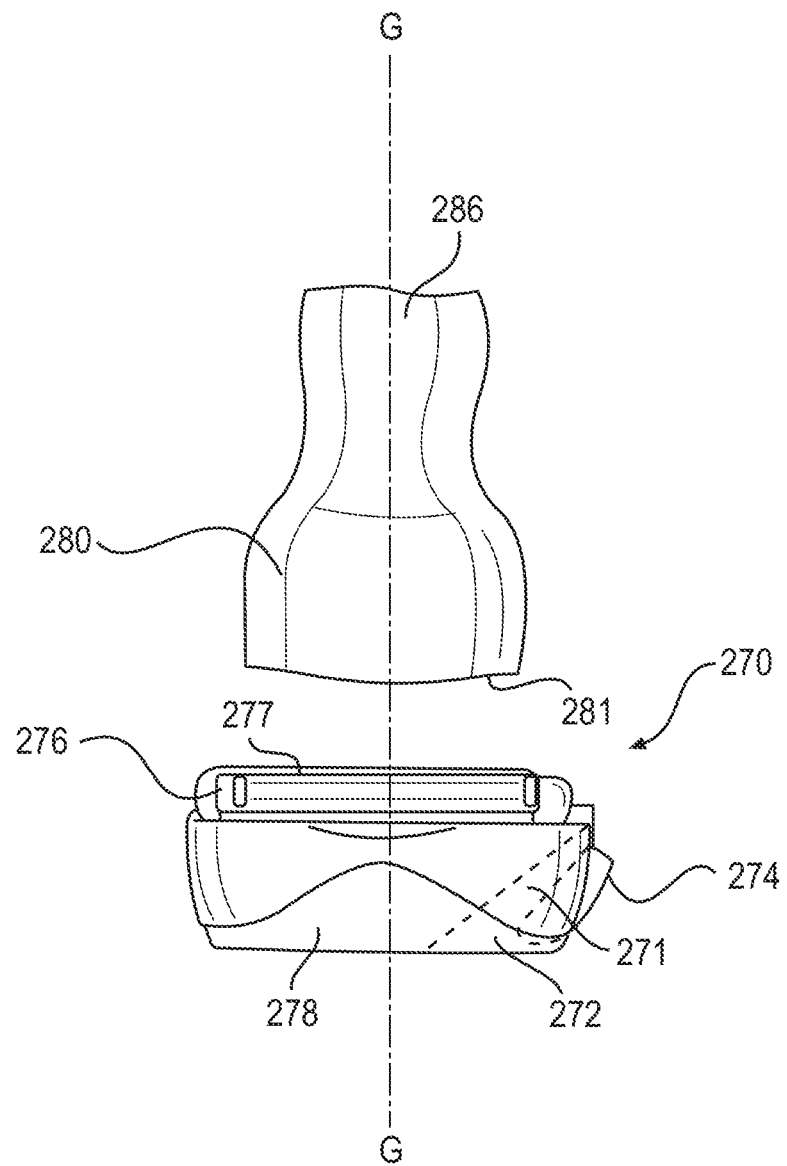
FIG. 7 is a profile view of another exemplary access guide.
Figure 8:
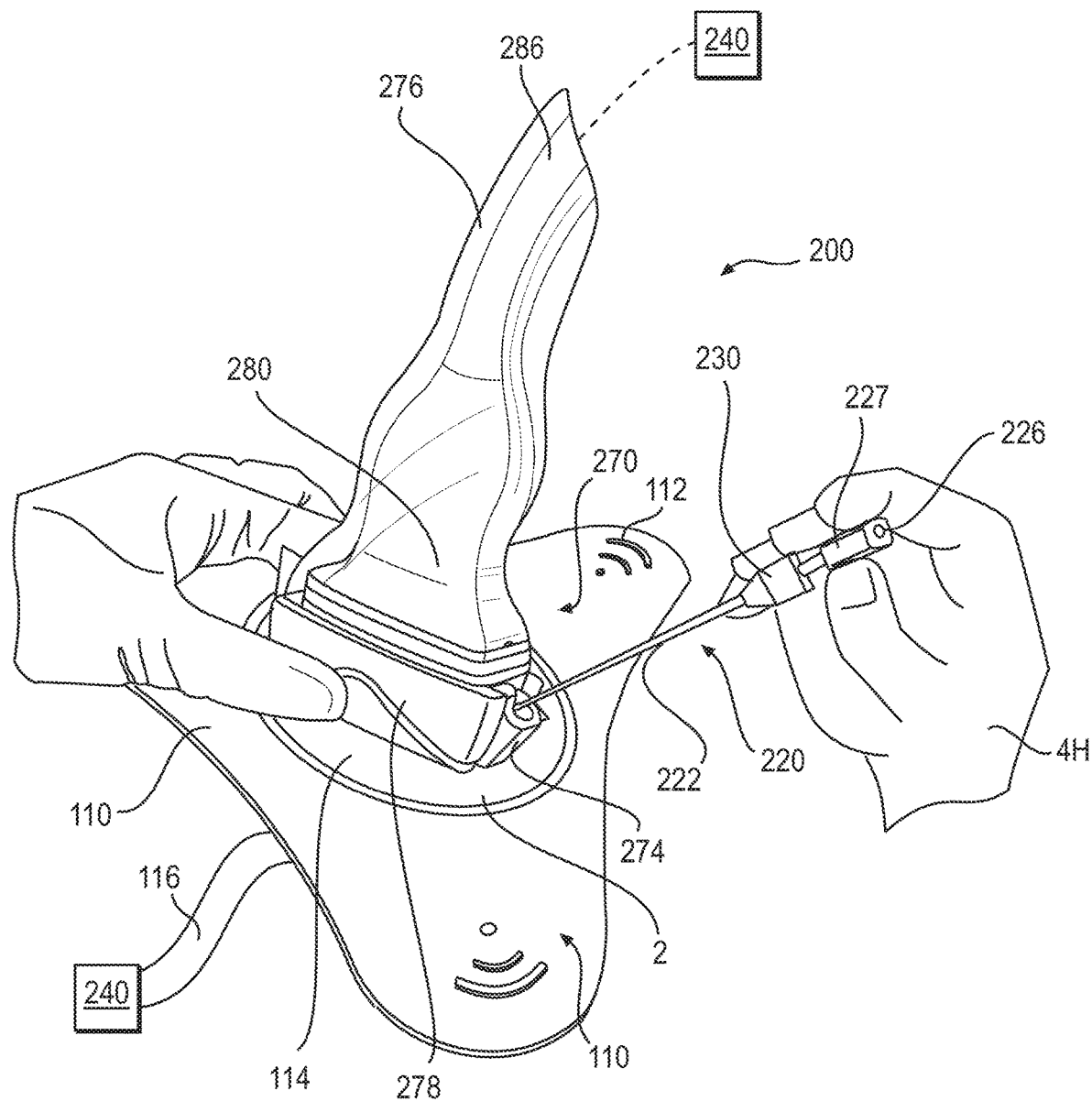
FIG. 8 is perspective view of the access guide of FIG. 7 together with an exemplary tracking pad in accordance with the present disclosure.

System 200 is similar to system 100, but with an alternate access guide 170, depicted FIGS. 7-8 as a guide 270. For convenience, system 200 is described with reference to pad 110. System 200 includes a needle 220 that, as before, has at least one beacon 230 operable with the plurality of sensors 112 on pad 110 to track the disposition of needle 120. Access guide 270 may not be attached to pad 110, and moveable within opening 114. As shown in FIG. 7, guide 270 is configured to receive a probe 280 and needle 220 so as to ensure that needle 220 will remain in the imaging plane of probe 280. Accordingly, the disposition of needle 220 may be tracked when its distal end is inserted into opening 114 of pad 110, through guide 270, along an insertion axis transverse to opening 114.

Access guide 270 is depicted in FIG. 7 as a removable attachment for probe 280, depicted as an ultrasonic probe. Guide 270 has at least one guide holster 274, an expandable cover 276, and a low friction base 278, each element being arranged along a guide axis G-G. Each holster 274 performs similarly to channel 171 and guide hole 172 of guide 170. For example, one side of access guide 270 may have a concave recess 271 (shown by dashed lines in FIG. 7) that, like channel 171, has a width greater than to the diameter of needle 20. Recess 271 is angled along guide axis G-G. Guide holster 274 is depicted as U-shaped channel element pivotally mounted to a distal end of recess 271 so as to form a guide hole 272 between a distal edge of recess 271 and a distal edge of holster 274. Holster 274 may be pivoted towards or away from axis G-G to adjust the angle of insertion of needle 120.

An assembled view of system 200 is provided in FIG. 8. As shown, a distal end 281 of probe 280 (FIG. 7) is attached to a proximal facing surface 277 of guide 270 (FIG. 7) by any known means, resulting in a joint therebetween. Probe 280 may, for example, be snapped onto guide 270. To maintain sterility, cover 276 of FIG. 8 has been expanded over the joint from proximal facing surface 277. Cover 276 may, for example, be unrolled from surface 277 to cover the joint. A distal end 224 of needle 220 is inserted into holster 274. In contrast to above, needle 220 has a proximal end 226 with an interface 227 engageable with a hand 4H. Low friction base 278 is provided to eliminate the need for additional lubricant between guide 270 and the surface of body 2. Base 278 may, for example, be formed entirely of a low friction or lubricous material, such as a solidified hydrogel.

Pad 110, similar to pad 10, utilizes a cable 116 as a power source and transceiver. Probe 280 utilizes a cable 286 extending therefrom for a similar purpose. Accordingly, as shown in FIG. 8, cable 116 may be used to communicate a first set of motion signals from plurality of sensors 112 to a processor 240, while cable 286 is used to communicate a second set of motion signals from probe 280 to processor 240.

Figure 9:
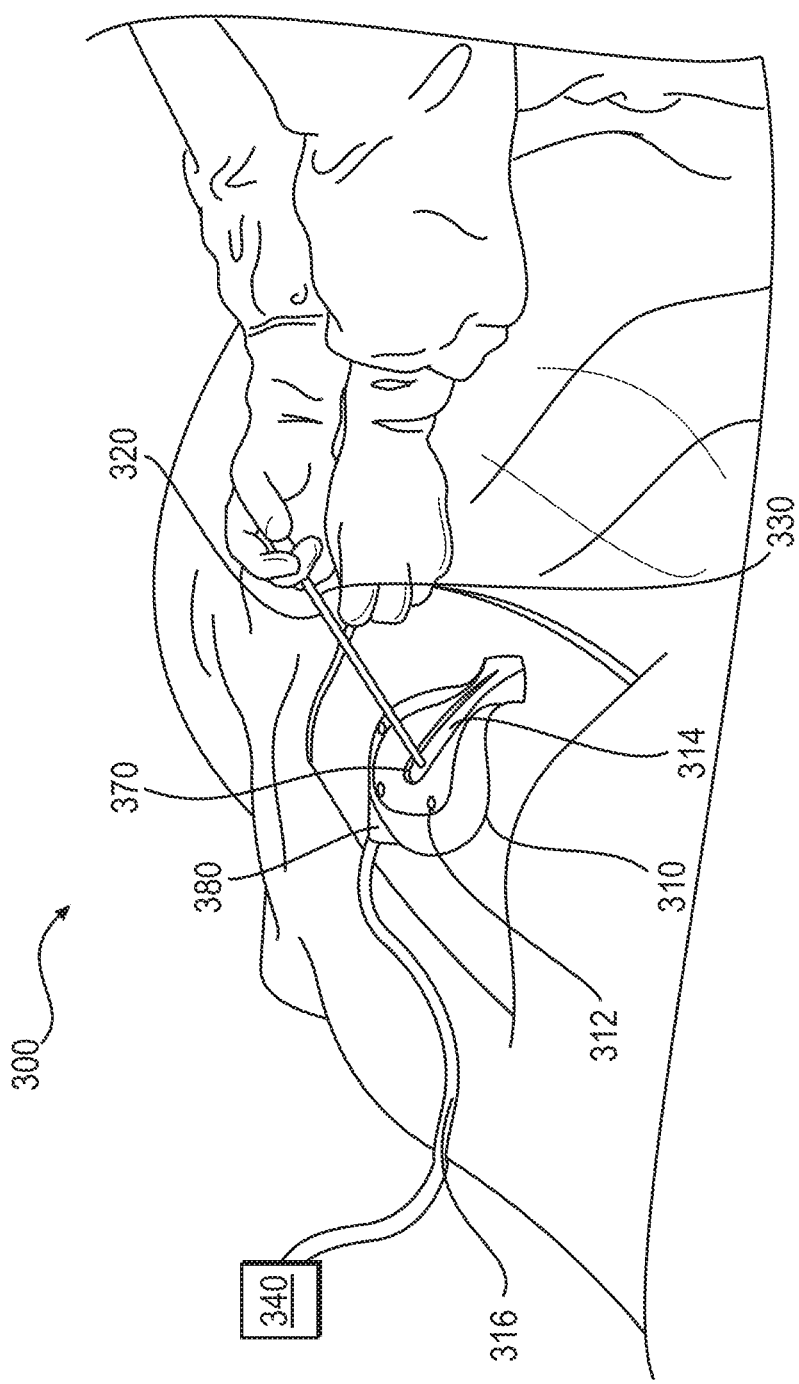
FIG. 9 is a perspective view of yet another exemplary system according to the present disclosure, the system comprising a tracking pad, an access guide integral with the tracking pad, and a needle.

System 300 is depicted in FIG. 9 as comprising a tracking pad 310 and a needle 320. Pad 310, similar to above, has a plurality of sensors 312 and at least one guiding opening 314. An access guide 370 and a probe 380 are integrally associated with pad 310, thereby allowing system 300 to match the capabilities of system 100 or 200. Needle 320 (FIG. 9) has at least one beacon 330 operable with the plurality of sensors 312 to track the disposition of needle 320 when a distal end of needle 320 is inserted into opening 314, through access guide 370, along an insertion axis transverse to opening 314. Probe 380 is depicted as an ultrasonic probe.

As shown in FIG. 9, guiding opening 314 is depicted as an elongated slot. Probe 380 is attached to pad 310 such that an imaging plane of probe 380 is aligned with guiding opening 314. Access guide 370 is defined by the sidewalls of opening 314, which are sloped towards body 2 so that needle 320 may be angled therein. The plurality of sensors 312 may be arranged in a triangular formation about guiding opening 314, as shown. Probe 380 of FIG. 9 is attached to both pad 310 and a cable 316. In contrast to above, a single cable 316 may serve as a power source and transceiver for each element of system 310. Accordingly, a shown in FIG. 9, cable 316 may be used to communicate a first set of motion signals from the sensors 312 to a processor 340, and a second a second of motion signals from probe 380 to processor 340.

Methods 50 and 60 described above may be used with systems 100, 200, 300. For tracking method 50, step 51 (FIG. 4A) may comprise placing a tracking pad 110 or 310 adjacent body 2. For system 100, step 51 may further comprise attaching access guide 170 to pad 110 (FIG. 5A-B); whereas, for system 200, step 51 may further comprise placing access guide 270 within guiding opening 114 (FIG. 7). Step 52 (FIG. 4B) may be used to locate a distal end 124, 224, or 324 of needle 120, 220, or 320 inside of guiding opening 114 or 314 at an insertion point adjacent the body 2. For systems 100 or 200, step 52 may further comprise passing the distal end 124 or 224 of needle 120 or 220 through guide opening 172 or 272 (FIG. 5A-B or 7). Step 53 (FIG. 4A) may be used track the actual disposition of needle 120, 220, or 320 relative to opening 114 or 314.

For tracking method 60, the steps 61 and 62 (FIG. 4B), for example, may be used establish a target insertion point for the distal end 124, 224, or 324 of needle 120, 220, or 320 within guiding opening 114 or 314, and determine a target disposition for needle 120, 220, or 320 (FIGS. 5-9). Method step 63 (FIG. 4B) may be used to place the distal end 124, 224, or 324 of needle 120, 220, or 320 at the target insertion point. For systems 100 and 200, step 63 may comprising inserting the distal end 124, 224, or 324 of needle 120 or 220 into a guide hole 172 or 272 via a channel 171 or 271 (FIG. 5A-B or 7-8); whereas, for system 300, step 63 may comprise inserting the distal end 124, 224, or 324 of needle 320 through guiding opening 314 (FIG. 9). In addition, or alternatively, step 64 (FIG. 4B) may be used to align needle 120, 220, or 320 with the target disposition. For systems 100 or 200, step 64 may further comprise moving access guides 170 or 270 relative to pad 110, moving probes 180 or 280 relative pad 110, and/or moving needle 120 or 220 relative to access guides 170 or 270 (FIG. 5A-B or 7-8). Step 65 (FIG. 4B) may, as before, be used to insert the distal end 124, 224, or 324 of needle 120, 220, or 320 into the body 2 in accordance with the target disposition.

Figure 10:
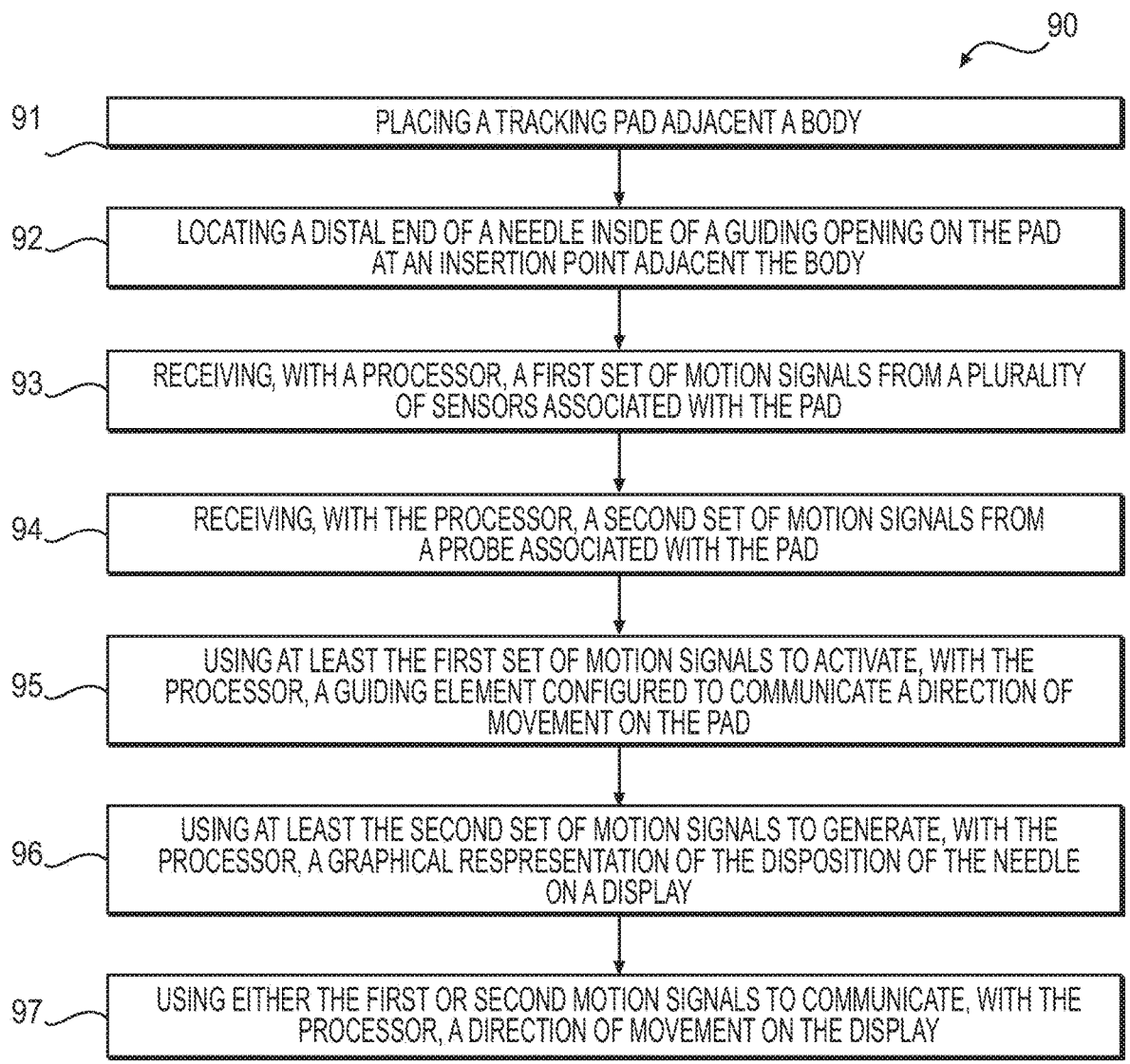
FIG. 10 depicts an exemplary set of method steps.

Another method 90 is disclosed with respect to systems 100, 200, and 300. Method 90 may comprise a step 91 (FIG. 10) for placing a tracking pad 110 or 310 adjacent a body 2; and a step 92 (FIG. 10) for locating a distal end of a needle 120, 220, or 320 inside of a guiding opening 114 or 314 on pad 110 or 310 at an insertion point adjacent body 2 (FIGS. 5-9). Another step 93 (FIG. 10) may comprise receiving, with a processor 140, 240, or 340, a first set of motion signals from a plurality of sensors 112, 212, or 312 associated with pad 110 or 310. Another step 94 (FIG. 10) may comprise receiving, with processor 140, 240, or 340, a second set of motional signals from a probe 180, 280, or 380 associated with pad 110 or 310 (FIGS. 5-9). Method 90 may further comprise a step 95 (FIG. 10) for using at least the first set of motion signals to activate, with processor 140, 240, or 340, a guiding element (e.g., guiding element 118 of FIG. 5B) configured to communicate a direction of movement on pad 110 or 310. Another step 96 (FIG. 10) may comprise using at least the second set of motion signals to generate, with processor 140, 240, or 340, a graphical representation (such as representation 184 of FIG. 6) of the disposition of needle 120, 220, or 320 on a display (such as display 185 of FIG. 6). Yet another method step 67 (FIG. 10) may comprise using either the first or second motion signals to communicate, with the processor 140, 240, or 340, a direction of movement on the display, for example, by overlaying a directional arrow "D" thereon.

Alternative aspects system 100, 200, and 300 are also disclosed, each aspect being part of the present disclosure. Numerous alternative aspects for system 1 have been described above, any of which may be incorporated into systems 100, 200, or 300. System 100, for example, is described with an access guide 170 pivotally and rotationally mounted to pad 110 (FIGS. 5A-B). These movements may be augmented by a locking device or a ratcheting mechanism, on either track 119 or protrusions 175A, 175B, so that the position of guide 170 may be fixed relative to opening 114. System 200 is similarly described with an access guide 270 having a holster 274 pivotally mounted thereto (FIGS. 7-8). This movement may be similarly augmented by a locking device, a ratcheting mechanism, or a biasing element so that the position of holster 274 may be fixed, or biased, relative to guide 270.

A self-sealing membrane may be incorporated into systems 100, 200, and 300. For example, in systems 100 or 300, such a membrane may be attached to pad 110 or 310, as above with pad 10. For system 200, a similar membrane on base surface 270C of access guide 270 (FIG. 5B). Guide 270 of system 200 is described with a base 278 (FIGS. 7-8) made of a lubricious material that allows for movement relative to body 2. Base 278 may, alternatively, have an internal reservoir of hydrogel, or like substance, and one or more distally directed output ports, wherein the hydrogel is expelled from said output ports by application of a compressive force to the sides of base 278.

Each of probes 180, 280, and 380 have been described as an ultrasonic probe, although this is not required. For example, any probing technology may used to generate a motion signal, including those base on light, x-rays, microwaves, or like technologies. Any such probing technology may be combined with any sensing technology described herein. Although described as a single probe, a plurality of probes may also be used. For example, probe 380 of system 300 (FIG. 9) may be depicted as a plurality of probes configured to provide a three dimensional representation of needle 320 in body 2. The motion signals output from sensors 312 may be used to generate aspects of this three dimensional representation, as described above.

Various cables 116, 216, 286, and 316 have been described as either a power source or transceiver for systems 100, 200, or 300. Similar to above, any aspect of pad 100, 200, or 300 may be comprise a wireless transceiver or internal power source so as to modify or eliminate these cables.

While principles of the present disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the present disclosure is not to be considered as limited by the foregoing description.

We claim:

1. A guidance method, the method comprising:
placing a tracking pad adjacent a body, the tracking pad including a guiding opening and a plurality of sensors;
locating a distal end of a needle inside of the guiding opening at an insertion point adjacent the body, the needle including at least one beacon;
operating the plurality of sensors with the at least one beacon to track an actual disposition of the needle;
establishing a target disposition for the needle;
moving the needle in a direction of movement to synchronize the actual disposition with the target disposition; and
inserting the distal end of the needle into the body along an insertion axis,
wherein the guiding opening prevents fluids from leaking into or out of the body.

2. The method of claim 1, wherein the tracking pad has a marking element configured to establish a target insertion point, inside the guiding opening of the pad, for the distal end of the needle, and wherein the method further comprises:
establishing the target insertion point; and
placing the distal end of the needle adjacent the target insertion point.

3. The method of claim 2, wherein the plurality of sensors are configured to track an actual insertion angle of the needle relative to the guiding opening, and wherein the method further comprises:
establishing a target insertion angle for the needle; and
moving the needle so as to align the actual insertion angle with the target insertion angle.

4. The method of claim 3, wherein the plurality of sensors are configured to track a distance between the guiding opening and the distal end of the needle, and wherein the method further comprises:
establishing a target distance between the guiding opening and the distal end of the needle; and
inserting the distal end of the needle into the body until the target distance is obtained.

5. The method of claim 4, further comprising:
after moving the needle in a direction of movement to synchronize the actual disposition with the target disposition, calibrating the plurality of sensors to define the target distance so as to align the actual insertion angle with the target insertion angle.

6. The method of claim 2, wherein the marking element projects at least two beams of light into the guiding opening, and the target insertion point is defined by a point of intersection between the at least two beams of light.

7. The method of claim 1, further comprising:
transmitting the actual disposition of the needle to a processor;
receiving the target disposition for the needle from the processor; and
indicating a direction of movement for the needle with a guiding element associated with the tracking pad.

8. The method of claim 7, wherein the guiding element displays the actual disposition and the target disposition.

9. The method of claim 7, wherein the guiding element indicates the direction of movement via a plurality of indicators on the tracking pad.

10. A guidance method, the method comprising:
placing a tracking pad adjacent a body, the tracking pad including a guiding opening and a plurality of sensors;
locating a distal end of a needle inside of the guiding opening at an insertion point adjacent the body;
receiving, with a processor, at least one motion signal from the plurality of sensors;
tracking, with a processor, the actual disposition of the needle;
establishing a target disposition for the needle;
moving the needle in a direction of movement to synchronize the actual disposition with the target disposition; and
inserting the distal end of the needle into the body along an insertion axis.

11. The method of claim 10, wherein the tracking pad has a marking element configured to establish a target insertion point, inside the guiding opening of the pad, for the distal end of the needle, and wherein the method further comprises:
establishing, with the processor, the target insertion point;
communicating, with the processor, the target insertion point to the marking element; and
indicating, with the marking element, the target insertion point.

12. The method of claim 11, further comprising placing the distal end of the needle adjacent the indicated target insertion point.

13. The method of claim 12, wherein the distal end of the needle is inserted into the body via the indicated target insertion point.

14. The method of claim 13, further comprising:
before moving the needle in the direction of movement to synchronize the actual disposition with the target disposition, indicating, with the guiding element, the direction of movement for aligning the needle with the target disposition.

15. The method of claim 14, wherein the guiding element further comprises a plurality of indicators on the tracking pad, each indicator being configured to indicate the direction of movement.

16. The method of claim 12, wherein the plurality of sensors are configured to track an actual insertion angle of the needle relative to the guiding opening, and wherein the method further comprises:
establishing a target insertion angle for the needle; and
moving the needle so as to align the actual insertion angle with the target insertion angle.

17. The method of claim 16, wherein the plurality of sensors are configured to track a distance between the guiding opening and the distal end of the needle, and wherein the method further comprises:
establishing a target distance between the guiding opening and the distal end of the needle; and
inserting the distal end of the needle into the body until the target distance is obtained.

18. The method of claim 10, wherein establishing the target disposition for the needle comprises:
determining, with the processor, the target disposition; and
communicating, with the processor, the target disposition to a guiding element associated with the tracking pad.

19. A guidance method, the method comprising:
placing a tracking pad adjacent a body, the tracking pad including a guiding opening and a plurality of sensors;
locating a distal end of a needle inside of the guiding opening at an insertion point adjacent the body, the needle including at least one beacon;

receiving, with a processor, a first set of motion signals from the plurality of sensors associated with the tracking pad;

receiving, with the processor, a second set of motion signals from a probe associated with the tracking pad;

using the first set of motion signals to activate, with the processor, a guiding element configured to communicate a direction of movement on the pad;

using the second set of motion signals to generate, with the processor, a representation of a disposition of the needle on a display; and using the first set of motion signals and/or the second set of motion signals to communicate, with the processor, a direction of movement on the display.

* * * * *